US005519057A

United States Patent [19]
Loew et al.

[11] Patent Number: 5,519,057
[45] Date of Patent: May 21, 1996

[54] IBUPROFEN-CONTAINING MEDICAMENT

[75] Inventors: Dieter Loew, Wuppertal; Otto Schuster; H. Lukas, both of Frankfurt, all of Germany

[73] Assignee: Johnson & Johnson—Merck Pharmaceuticals Co., N.J.

[21] Appl. No.: 405,680

[22] Filed: Sep. 11, 1989

Related U.S. Application Data

[63] Continuation of Ser. No. 119,028, Nov. 10, 1987, Pat. No. 4,877,620.

[30] Foreign Application Priority Data

Nov. 14, 1986 [DE] Germany ............... 36 39 038.0

[51] Int. Cl.$^6$ ............................................. A61K 31/19
[52] U.S. Cl. ..................... 514/568; 514/557; 514/570; 514/947; 514/960; 514/962
[58] Field of Search .................... 514/570, 557, 514/568, 947, 960, 962

[56] References Cited

U.S. PATENT DOCUMENTS

| | | |
|---|---|---|
| 4,555,524 | 11/1985 | Gruber et al. . |
| 4,690,823 | 9/1987 | Lohner et al. . |
| 4,877,620 | 10/1989 | Loew et al. .............................. 424/45.1 |

OTHER PUBLICATIONS

The American College Dictionary—1970 p. 756.
Biochemical Pharmacology, vol. 35, No. 19 (Oct. 1985), pp. 3403–3405, Pergamon Journals Ltd., K. Williams et al., "The Steroselective Uptake of Ibuprofen Enantiomers into Adipose Tissue".
Current Medical Research and Opinion, vol. 3, No. 8 (1975), p. 552, S. S. Adams et al., "The Optical Isomers of Ibuprofen" month unavailable.
J. Pharm. Pharmacol., vol. 28 (1976), pp. 256–257, S. S. Adams et al., "Pharamacological Difference Between the Optical Isomers of Ibuprofen: Evidence for Metabolic Inversion of the (−)-Isomer" month unavailable.
Journal of Pharmaceutical Sciences, vol. 56 (1967), p. 1686, S. S. Adams et al., "Some Biological Properties of 2-(4-Isobutylphenyl)-Propionic Acid" month unavailable.
Biochemical and Biophysical Research Communications, vol. 61, No. 3 (1974), pp. 833–837, W. J. Wechter et al., "Enzymatic Inversion at Saturated Carbon: Nature and Mechanism of the Inversion of R(−)p-iso-Butyl Hydratropic Acid" month unavailable.
J. Pharm. Pharmacol., vol. 35 (1983), pp. 693–704, Andrew J. Hutt et al., "The Metabolic Chiral Inversion of 2-Arylpropionic Acids—A Noval Route with Pharmacological Consequences" month unavailable.
Clinical Pharmacokinetics, vol. 9 (1984), pp. 693–704, Andrew J. Hutt et al., "the Importance of Stereo-Chemistry in the Clinical Pharmacokinetics of the 2-arylproprionic Acid Non∝Steroidal Anti-Inflammatory Drugs" month unavailable.

The Journal of Pharmacology and Experimental Therapeutics, vol. 232, No. 3 (1985), pp. 636–643, J. W. Cox et al., "Ibuprofen Stereoisomer Hepatic Clearance and Distribution in Normal and Fatty in Situ Perfused Rat Liver" month unavailable.
American Society for Clinical Pharmacology & Therapeutics, vol. 42, No. 2 (Feb. 1987), p. 200, PIIL-7.
Clinical Pharmacology & Therapeutics, vol. 40, No. 1 (1986), pp. 1–7, Eugene M. Laska et al., "The Correlation Between Blood Levels of Ibuprofen and Clinical Analgesic Response" month unavailable.
Chemical Abstracts, vol. 106 (1987), Abstract No. 66922r (Daicel Chemical Industries, Ltd.) month unavailable.
Physicians' Desk Reference, 40th Edition, (1986), pp. 1854–1855, Edward R. Barnhart month unavailable.
Xenobiotica, vol. 3, No. 9 (1973), pp. 589–598, R. F. N. Mills et al., "The Metabolism of Ibuprofen" month unavailable.
Journal of Pharmaceutical Sciences, vol. 64, No. 5 (1975), pp. 798–801, Garrett J. Vangiessen et al., "GLC Determination of Ibuprofen [dl-2-(p-Isobutylphenyl)-Propionic Acid] Enantiomers in Biological Specimens" month unavailable.
Journal of Pharmaceutical Science, vol. 65, No. 2 (Feb. 1976), pp. 269–273, D. G. Kaiser et al., "Isomeric Inversion of Ibuprofen (R)-Enantiomer in Humans".
Anti-Inflammatory and Anti-Rheumatic Drugs, Eds. Rainsford and Path, CRC Press Inc., Boca Raton, Fla. (1985), p. 172, Anthony C. Allison et al., "Naproxen" month unavailable.
Angew, Chem. Internat. Edit., vol. 11, No. 6 (1972), pp. 460–472, T. Y. Shen, "Perspectives in Nonsteroidal Anti--Inflammatory Agents" month unavailable.
Nonsteroidal Anti-Inflammatory Agents, Chapter 62 in Burger's Medical Chemistry, 4th Edition, Part III, Wiley Interscience, New York (1981), pp. 1205–1271, T. Y. Shen month unavailable.
Br. J. Clin. Pharmac., vol. 19 (1985), pp. 669–674, E. J. D. Lee et al., "Stereoselective Disposition of Ibuprofen Enantiomers in Man" month unavailable.
The Journal of Pharmacology and Experimental Therapeutics, vol. 148. No. 3 (1965), pp. 373–379, Charles A. Winder et al., "Nociceptive Thresholds as Affected by Parenteral Administration of Irritants and Various Antinociceptive Drugs" month unavailable.
Proceedings of the Society of Experimental Biology and Medicine, vol. 118, (1965), pp. 763–766, H. Blumberg et al., "Use of Writhing Test for Evaluating Analgesic Activity of Narcotic Antagonists" month unavailable.

(List continued on next page.)

*Primary Examiner*—Jacqueline V. Howard
*Attorney, Agent, or Firm*—Woodcock Washburn Kurtz Mackiewicz & Norris

[57] ABSTRACT

An ibuprofen-containing medicament which contains ibuprofen only in the (S)-(+)-form is disclosed. (S)-(+)ibuprofen is more than twice as active as the racemate which has until now been used in the treatment of rheumatism. This permits reduction of the quantity of active ingredient and the size of the tablets or dragees.

24 Claims, No Drawings

OTHER PUBLICATIONS

Journal of Pharmaceutical Sciences, vol. 73, No. 11 (Nov. 1984), pp. 1542–1544, E. J. D. Lee et al., American Pharmaceutical Association, "Liquid Chromatographic Determination and Plasma Concentration Profile of Optical Isomers of Ibuprofen in Humans".

Remington's Pharmaceutical Sciences, 15th Edition (1975), Mack Publishing Company, Easton, Pennsylvania 18042 Chapter 59, p. 1054, "John E. Humans" month unavailable.

Caldwell et al., "The Metabolic Chiral Inversion and Dispositional Enantioselectivity of the 2-Arylpropionic Acids and Their Biological Consequences", vol. 37, No. 1, pp. 106–114 (1988) month unavailable.

K. M. Williams and R. O. Day, AAS 17, Nonsteroidal Anti–Inflammatory Drugs–Basis for Variability in Response c. 1985 Berkhauser Verlag, Basel month unavailable.

IBUPROFEN-CONTAINING MEDICAMENT

This is a continuation of application Ser. No. 119,028, filed on Nov. 10, 1987, now U.S. Pat. No. 4,877,620.

Non-steroidal anti-rheumatics (NSAR) are used to a great extent in the treatment of rheumatism. Extensive results show that the NSAR are inhibitors of prostaglandin formation and that the therapeutic effect of the NSAR correlates with this inhibitory effect.

Alongside the required effects, i.e. anti-phlogistic, analgetic and in some cases antipyrretic properties, all NSAR have unwanted side effects. Among these are effects on the gastro-intestinal tract, stomach ulcer formation, diarrhea, sodium retention, oedema formation, and kidney damage as well as effects on the central nervous system and respiratory tract. Besides these general side effects, specific unwanted side effects, especially allergies, can be caused by NSAR.

The NSAR, particularly those prescribed for rheumatic illnesses, must, in order to be effect and achieve the required relief for the patient, be administered in a sufficient dose. At high dosages which are often required to combat acute pain, and with a prolonged treat- ment which, especially with rheumatics, is often un- avoidable, the dangers of the unwanted side effects increase.

Ibuprofen, i.e. 2-(4-Isobutylphenyl)-propionic acid with the structural formula is a tried and tested NSAR from the group of phenyl propionic acid derivatives that has shown itself to be effective in inhibiting prostaglandin synthesis in experiments with animals with inflammation. In therapy of humans, ibuprofen reduces pain, swelling and fever caused by inflammation. It shows the usual unwanted side effects of NSAR. The recommended dosage range for oral and rectal administration lies, for maximum individual doses of 800 mg, between 1200 and a maximum of 2400 mg ibuprofen per diem and is thus, in comparison to other NSAR, especially the tried and tested compounds Diclofenac and Indometacin, for which median daily doses of 0.2 or 0.1 g are recommended, relatively high, the recommended median daily dose for ibuprofen being more than 1 g. The individual dosage forms in tablets or dragees are correspondingly large and not less than 200 mg; as a rule they lie between 400 and 600 mg since a sufficient quantity of the active ingredient is necessary to achieve the maximum plasma level. These large tablets or dragees are regarded as being a disadvantage since they are often hard to swallow. Smaller dosage forms which have to be taken more often or several at a time are not recommended because of the strain on the patient which this causes. The large dosage forms make a sustained-release formulation more difficult as this requires inclusion of additional substances in the dosage form.

Ibuprofen has an asymmetric carbon atom and is present as the racemate in the therapeutically-used form. It is known that for many pharmaceutically-active ingredients having one or more asymmetric carbon atoms that one enantiomeric form is often more effective or even much more effective than the other enantiomeric form; in isolated instances the pharmacological activity is accounted for by only one of the enantiomers. It is known that (R)-(−)-ibuprofen has substantially less pharmacological activity than (S)-(+)-ibuprofen. Since, however, the ineffective (R)-(−)-enantiomer is converted to the active (S)-(+)-enantiomer in vivo, as has been proved by analysis of ibuprofen metabolites excreted in the urine, no therapeutic advantage has until now been expected from the use of the (S)-(+)-form instead of the racemate and a separation of the dextro rotatory form from the laevo rotatory form has not been thought to be necessary.

It has now been found that, contrary to established opinion, according to which the ibuprofen-racemate was the most suitable therapeutically-active form since the inactive (R)-(−)-enantiomer was converted into the active (S)-(+)-enantiomer in humans, that the (S)-(+)form of ibuprofen, i.e. in the absence of the (R)-(−)form has a substantially greater pharmacological potential than was anticipated. The present invention is based on this recognition.

The invention relates to an ibuprofen-containing medicament and is characterized in that in the medicament ibuprofen is only present as the (S)-(+)-enantiomer. It was not to be expected that by the sole use of the (S)-(+)-enantiomer a substantial reduction of dosage would be possible, since it was known that the as such largely inactive (R)-(−)-ibuprofen was converted into the active (S)-(+)-ibuprofen in humans. It was, however, surprisingly found that the same analgetic activity caused by a given dose of racemic ibuprofen can not only be achieved by half the dose of (S)-(+)-ibuprofen, but that even less than half as much (S)-(+)-ibuprofen as racemic ibuprofen is required to give a given analgetic activity. This result is, on the basis of observations until now on the mechanism of action of NSAR, particularly ibuprofen, extremely surprising. These findings originate from analgesia tests on monkeys which, on the basis of their phylogenetic position, are most similar to humans in their metabolic characteristics. These results could also be shown in humans.

This surprising result could be explained on the basis that the (S)-(+)-ibuprofen formed by inversion of the inactive (R)-(−)-form in humans is, due to its formation in the liver and due to all other flow kinetics, quickly metabolically inactivated and excreted. Thus the (S)-(+)-form arising by metabolism from the (R)-(−)-form cannot arrive at the site at which its activity is required, i.e. the inflammed tissues, by the necessary distribution processes. On the other hand the presence of the (R)-(−)-form can supress the transportation of the (S)-(+)-form to the inflammed tissue.

In order to achieve sufficient pharmacological effect in humans it is of decisive importance that pure (S)-(+)-enantiomer is used, since only then is a sufficiently high concentration in the blood achieved quickly enough, this being necessary for quick distribution to the site of action. After administration of the (S)-(+)-form a substantially higher concentration at the site of action is achieved than when the racemate or (R)-(−)-form is applied.

This is of substantial therapeutic significance since the reduction of the effective dose according to the invention also naturally reduces the unwanted side effects. The (R)-(−)-form which is practically in the racemate as ballast is left out along with the side effects caused by this 50% portion of the racemate. In addition to this, the specific enzyme system (Co-A-derivative) required for the partial inversion of the (R)-(−)-form into the (S)-(+)-form occurring in the organism is no longer required; it is not needed for the metabolism of the (S)-(+)-form. Since this enzyme system is essential for vital metabolic and detoxification processes, it is advantageous that it is no longer required on use of the (S)-(+)-form as sole ibuprofen active ingredient since it thus remains completely available for the detoxification and metabolic processes.

There is a reverse synergism here. (S)-(+)-ibuprofen shows, at half the dose, a greater activity than the corresponding racemate. Thus it is possible to use a dosage form with less than half the quantity that was until-now required to achieve a given result using the racemate. The individual dosage forms, i.e. tablets or dragees, etc., can be made correspondingly smaller. On the contrary, at the same size of tablet or drageet twice the quantity of active ingredient can be formulated. Since, however, the inactive (R)-(−)-form, which until now had to be "carried" in the racemate not only caused a large volume of tablet or dragee to have to be maintained, but also competed with the (S)-(+)-enantiomer also present, the actual quantity of the active ingredient can be less than half the quantity of the racemate.

The 1200 to 2400 mg average daily dose thought necessary until now can at least be halved. The possible reduction of the dosage form also makes sustained-release formulation possible which until now was difficult and not carried out in practice. Two-stage tablets in which the (S)-(+)-enantiomer is present in sustained-release form in combination with non-sustained-release form may now also be more easily formulated; such dosage forms are no longer excessively voluminous and thus inapplicable for the patients.

The formulation of (S)-(+)-ibuprofen into tablets, dragees and other formulations suitable for oral application is carried out in a conventional manner using known carriers and diluents. Such formulations are known in galenism and can also be used in the present invention. This similarly applies for formulations for rectal administration. All the galenic preparations have the common feature, however, that, since they contain ibuprofen in the (S)-(+)-form only they are equally effective with a smaller quantity of the active ingredient, or, in the event that they have the same concentration of active ingredient as the racemate form, then they have more than twice the pharmacological activity of the racemate form.

For injectable preparations it is advantageous to formulate (S)-(+)-ibuprofen in combination with an amino acid. The solubilization is improved in this way.

(S)-(+)-ibuprofen is obtained by a conventional optical resolution. For example, optically active phenyl ethyl amine can be used for this purpose. (R)-(+)-phenyl ethyl ammonium-(R)-(–)-ibuprofemate and (S)-(–)-phenyl ethyl ammonium-(S)-(+)-ibuprofemate are less soluble than their diastereoisomers and can therefore be separated from these. By repeated recrystallization of the more difficultly soluble diastereoisomers from an ethyl acetate/ethanol mixture, the diastereoisomers can be purified. By acid cleavage with, for example hydrochloric acids and subsequent extraction with ether, the corresponding ibuprofen enantiomer is obtained from the diastereoisomeric compound and produced in pure form.

Conventionally used adjuvants such as lactose, microcrystalline cellulose, powdered cellulose, maltodextrin or calcium hydrogen phosphate are suitable for the production of tablets, dragees and film tablets; they are used in a quantity of 10 to 80%.

As tablet disintegrants can be used, for example, (in a concentration of 2 to 8%) insoluble poly(1-vinyl-2-pyrrolidone), cross-linked sodium carboxymethyl cellulose, sodium carboxymethyl starch, formaldehyde casein, alginate and conventionally used starches.

As lubricant and separating agent there can be used metal soaps and talcum in a concentration of ca. 1 to 5%.

As a further adjuvant, highly dispersed silicon dioxide can be used.

EXAMPLE 1

Ibuprofen, tablets
1 tablet contains in mg

| | |
|---|---|
| (S)-(+)-ibuprofen* | 300.0 |
| insoluble polyvinyl pyrrolidone | 20.0 |
| microcrystalline cellulose | 150.0 |
| magnesium stearate | 10.0 |

*The active ingredient can be varied from 20 to 800 mg/tablet. The adjuvants are correspondingly reduced or increased.

The tablets can also be produced as film tablets.

EXAMPLE 2

Ibuprofen, capsules
1 sustained-release capsule contains in mg

| | |
|---|---|
| (S)-(+)-ibuprofen* | 200.0 |
| (S)-(+)-ibuprofen* sustained-release | 200.0 |

*The active ingredient in non-sustained-release form as well as in sustained-release form does not have to be present in a 1:1 ratio; it can also be used in the ratio 1:0.5–1:4. The quantities of adjuvants required in these pellets vary in proportion to these changes in the amount of active ingredient.

The sustained-release pellets of (S)-(+)-ibuprofen contain, in addition to the 200 mg of active ingredient saccharose corn starch stearic acid poly(carboxymethyl) starch, sodium salt poly(1-vinyl-2-pyrrolidone) schellack talcum

EXAMPLE 3

Ibuprofen, suppositories
1 suppository contains in mg

| | |
|---|---|
| (S)-(+)-ibuprofen* | 450.0 |
| hard fat | 1891.0 |
| Tocopherol | 9.0 |

*In this preparation the amount of active ingredient can be varied from 20 to 800 mg; the necessary quantity of hard fat is correspondingly altered to achieve a suppository of 2.3 g.

EXAMPLE 4

Ibuprofen, injection solution
In a 3 ml capacity ampule 2 ml of solution having the following composition are contained:

| | |
|---|---|
| (S)-(+)-ibuprofen | 300 mg |
| dl-Lysine | 212 mg |

EXAMPLE 5

Ibuprofen, injection solution
In an-ampule of 3 ml capacity are contained 2 ml of a solution having the following composition:

| | |
|---|---|
| (S)-(+)-ibuprofen* | 300.0 mg |
| Meglumine | 258.7 mg |

*The quantity of active ingredient in these preparations can be varied from 200 to 500 mg; the adjuvants lysine and meglumine must be reduced or increased correspondingly. If necessary the quantity of the solvent, water, must be increased or the size of the ampule must be varied. The pH value of the injection solution should lie between 7.3 and 7.8.

EXAMPLE 6

Conventionally used adjuvants can be used in the preparation of salves.

| | |
|---|---|
| (S)-(+)-ibuprofen | 5.0 g |
| *Neo-PCL self emulsifying W/O | 25.0 g |
| Isopropyl myristate | 7.0 g |
| Magnesium sulfate-heptahydrate | 0.5 g |
| Phenylmercuryborate | 0.004 g |

*Neo-PCL self-emulsifying W/O is a non-ionic absorption base free of paraffin oil and vaseline.

(S)-(+)-ibuprofen is dissolved in a melt of Neo-PCL and isopropyl myristate at about 60° C.

Magnesium sulfate and the preservative are dissolved in water at 60° to 70° C.

The water phase is stirred into the fat phase and the finished salve mixed until it has cooled to <30° C.

Synergistically working emulsifier combinations based on a mixture of purified oleic acid and a high potency lanolin alcohol fraction with 36% PCL-liquid and PCL-solid.

EXAMPLE 7

Hard gelatin capsules (S)-(+)-ibuprofen is heated to 52° C. with polyethylene glycol 1500 in a ratio of 1:1. The resulting clear melt is stirred and cooled to ca. 40° C. 600 mg of the still clear melt is then filled into hard gelatin capsules. The content of active ingredient in these capsules thus amounts to 300 mg (S)-(+)-ibuprofen.

The content of active ingredient can easily be controlled by decreasing or increasing the quantity of previously prepared melt which is added to the hard gelatin capsule.

After the filling, the active ingredient-containing melt solidifies at about 32° C. in the capsule. Sealing of the hard gelatin capsule is not necessary. The capsules can be directly packed and stored.

Since the active ingredient in the capsules is a liquid at body temperature, the desired rapid resorption occurs which causes a rapid start of activity. The required high level of (S)-(+)-ibuprofen is achieved within a short period.

Liberation of the active ingredient (S)-(+)-ibuprofen from such a capsule occurs significantly more quickly than from a corresponding capsule which contains the same quantity of active ingredient but in crystalline form. Crystalline (S)-(+)-ibuprofen may, however, be dosed without adjuvants and without expensive processing. It is possible to dose the pure substance as a melt (melting point 52° C.). In this case, however, the in vitro liberation of the active ingredient occurs only sluggishly (retarded).

Evaluation of the Analgetic Activity of Ibuprofen

In this test the afferent nerves of the feet of female Rhesus monkeys were electrically stimulated. For the test four adult female Rhesus monkeys (macaca mulatta) were used.

The following active ingredients were used:

(S)-(+)-ibuprofen
(R)-(−)-ibprofen
(±)-ibuprofen
Acetylsalicylic acid

Methods

The monkeys were trained in such a way that they sat in chairs wearing an aluminium foil shoe during the test.

On the days when the test was carried out the monkeys were sat in these stools. One foot of each monkey was smeared with electrode gel and the aluminium shoe was fitted over it.

A Grass-stimulator (S 88) was connected to the monkeys via a multiple-way switch (the positive lead was connected to the aluminium shoe, the negative lead to the chair). An electrical stimulation, each time of 2 seconds duration with a frequency of 60 Hz was applied (the magnitude of stimulation was altered by adjusting the voltage supplied to the stimulator; the corresponding current was measured by means of an ammeter connected in series).

The stimulus required to achieve a stimulus threshold was determined. For this purpose the voltage was raised stepwise. The threshold voltage was taken as the lowest voltage at which bending of the toes or twisting of the foot occurred.

Before application of the medicament the animals were allowed to acclimatize for at least one hour. During this period the threshold voltage was determined at 10 minute intervals until steady readings were obtained.

Following the acclimatization period the carrier material or the active ingredient were orally administered. The threshold voltage required to effect a stimulus response in the foot of each monkey was determined at 30 minute intervals for 3 hours and then after 4 and 5 hours after administration of the active ingredient.

The observer and the stimulation apparatus were concealed behind a one-way mirror.

Each animal was treated with the following active ingredients in the given quantities:

| | |
|---|---|
| 1. (S)-(+)-ibuprofen | 50 mg/kg |
| 2. (R)-(−)-ibuprofen | 50 mg/kg |
| 3. (±)-ibuprofen | 50 mg/kg |
| 4. acetylsalicylic acid | 100 mg/kg |
| 5. carrier (0.5% carboxymethyl cellulose | |

Between the individual tests there was an interval of at least one week.

The active ingredients 1 to 4 were prepared for oral administration by suspending them in 1.0% w/v Tragacanth. The medicaments were prepared directly before use and administered in a dose of 4 ml/kg.

The results obtained are shown in Table 1.

Carrier

Oral administration of the carrier (1.0% Tragacanth) gave a small decrease of the threshold voltage required to achieve a response.

Acetylsalicylic acid

After administration of 100 mg/kg acetylsalicylic acid the threshold voltage required for a stimulus response was increased by something approaching 80%. This level of analgesia was achieved within 2 hours after administration of the active ingredient and remained above 60% throughout the duration of the test. Analgesia was assumed when the threshold voltage was 20% above the level required after administration of the carrier alone.

Ibuprofen

Oral administration of (R)-(−)-ibuprofen (50 mg/kg) gave no significant change in the threshold voltage. In contrast thereto oral administration of (S)-(+)-ibuprofen (50 mg/kg) gave an increase of the threshold voltage approaching 50%. This increase was achieved 90 minutes after administration and the threshold voltage remained elevated during the rest of the test period. After administration of ibuprofen racemate (50 mg/kg) the threshold voltage was increased by approximately 15%. This increase was achieved within 90 minutes and the level remained during the rest of the test period. Although the racemate only increased the threshold voltage by 15%, analgetic activity was assumed since the threshold voltage decreased after administration of the carrier only. The difference between the median change between ibuprofen racemate and carrier amounted to more than 20% for every time after 90 minutes with the exception of 150 minutes.

Discussion of Results

In the test animals (S)-(+)-ibuprofen had a notable analgesic effect which was maintained for several hours. The (R)-(−)-isomer was inactive and the racemate had a weak but long-lasting analgetic effect.

6 hours after application the areas under the plasma level curves (AUC) of the (S)-(+)-form after administration of the (S)-(+)-enantiomer are approximately a factor of 2.5 larger than after administration of the (R)-(−)-enantiomer. Only after this time period are equally high or higher levels

TABLE 1

Percentage change of the voltage required to achieve a stimulus response in the female Rhesus monkeys

| Treatment | Oral Dose (mg/kg) | Median percentage change in the threshold voltage at various times (h) after administration of the effective ingredient | | | | | | | |
|---|---|---|---|---|---|---|---|---|---|
| | | 0,5 | 1,0 | 1,5 | 2,0 | 2,5 | 3,0 | 4,0 | 5,0 |
| Carrier | — | −6,6 | −4,8 | −13,0 | −7,4 | −4,3 | −5,6 | −11,5 | −8,9 |
| (+)-S-Ibuprofen | 50 | +9,5 | +33,5* | +51,2* | +53,9 | +45,5 | +42,3 | +33,7 | +38,2 |
| (−)-R-Ibuprofen | 50 | −5,7 | +4,0 | +4,5 | +0,5 | −4,7 | −7,0 | −2,3 | −3,4 |
| (+)-Ibuprofen | 50 | +6,4 | +8,4 | +15,7 | +15,7 | +8,5 | +18,1 | +9,7 | +17,0 |
| Acetylsalicylic Acid | 100 | +35,8 | +56,6* | +41,4 | +80,4 | +74,6 | +72,8 | +66,1 | +59,8 |

Statistical analyses carried out using the Mann-Whitney U Test
*P < 0,05 compared to the carrier Percent change in the threshold voltage required to achieve a stimulus response in female rhesus monkeys which have been orally treated with (S)-(+)-ibuprofen, (R)-(−)-ibuprofen, (±)-ibuprofen, acetylsalicylic acid or with the carrier:

achieved after administration of the (R)-(−)-form than after administration of the (S)-(+)-form. Since these levels are less than 10% of the maximum level they no longer contribute to the required activity.

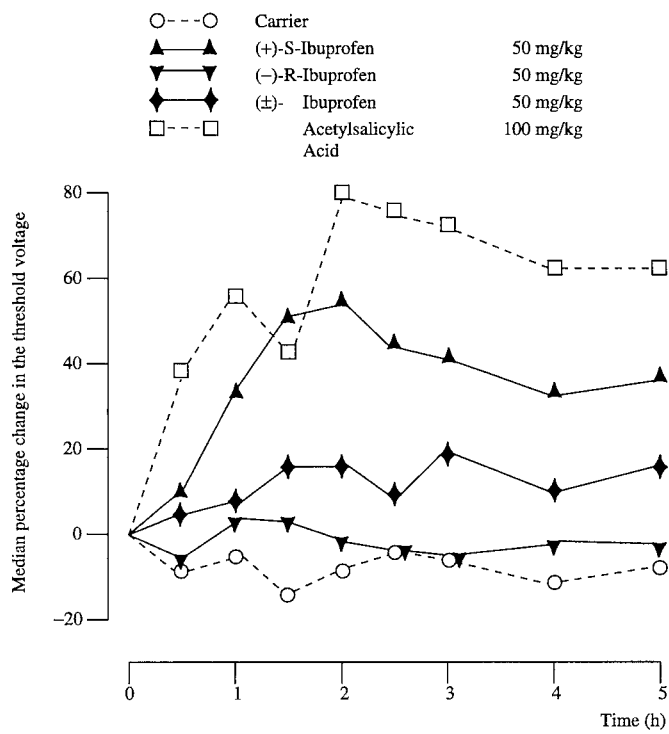

In a pilot run the human pharmaco kinetics of the ibuprofen forms was investigated. The maximal plasma levels of the active (S)-(+)-form lie, after oral administration of the (S)-(+)-enantiomer on average 4 to 5 times higher than after administration of the (R)-(−)enantiomer. Within the first 4 to Thus it can also be explained from a pharmaco kinetic point of view that within the known period of action of ibuprofen (ca. 6 hours) no effect can be expected from the (R)-(−)-form.

We claim:

1. The method of eliciting an onset-hastened and enhanced analgesic response in a human mammal suffering from pain and in need of such treatment, comprising administering to such organism a dosage onset-hastening/enhancing analgesically effective amount of the S(+) ibuprofen enantiomer, and said enantiomer being free of its R(−) ibuprofen antipode.

2. A pharmaceutical composition of matter adapted to elicit an onset-hastened and enhanced analgesic response in a mammalian organism in need of such treatment, said composition comprising a solid-state dosage onset-hastening/enhancing analgesically effective amount of the S(+) ibuprofen enantiomer, said enantiomer being free of its R(−) antipode, and a nontoxic pharmaceutically acceptable carrier or diluent therefor.

3. The pharmaceutical composition of matter according to claim 2, adapted for oral administration.

4. The pharmaceutical composition of matter according to claim 3, formulated as a tablet, caplet, pill or capsule.

5. A method of achieving quick analgesia and greater analgesic activity in a human experiencing pain comprising administering to such human a dosage amount of (S)(+)-ibuprofen enantiomer effective to achieve quick analgesia and greater analgesic activity in such human, said enantiomer being in the absence of the (R)(−)-form.

6. A pharmacological composition adapted to achieve quick analgesia and greater analgesic activity in a human experiencing pain, said composition comprising a dosage of an amount of (S)(+)-ibuprofen enantiomer effective to achieve quick analgesia and greater analgesic activity in such human, said enantiomer being in the absence of the (R)(−)-form, and a suitable carrier or diluent therefor.

7. In an ibuprofen-containing analgesic composition, the improvement in which quick analgesia and greater analgesic activity in a human experiencing pain can be achieved wherein said ibuprofen present is the (S)(+)-enantiomer form which has been separated from its (R)(−)-form by conventional optical resolution.

8. The composition of claim 7 wherein said conventional optical resolution comprises recrystallization and subsequent purification of less soluble diastereoisomers.

9. A pharmacological analgesic composition adapted to quickly achieve a high concentration in the blood of a human experiencing pain upon administration of said composition, said composition comprising a dosage amount of (S)(+)-ibuprofen enantiomer effective to quickly achieve a high concentration thereof in the blood of such human, said enantiomer having been separated from its (R)(−)-form by conventional optical resolution.

10. In a pharmacological composition suitable for administration to humans experiencing pain containing an analgesically effective dosage amount of ibuprofen, the improvement wherein said dosage amount is reduced by at least half while retaining at least comparable analgesic activity, which improvement comprises using as the sole ibuprofen ingredient the (S)(+)-ibuprofen enantiomer.

11. The method of claim 5 wherein said dosage amount of (S)(+)-ibuprofen enantiomer includes a suitable carrier or diluent therefor.

12. In a method of administering an ibuprofen-containing analgesic composition to a human experiencing pain, the improvement in which quick analgesia and greater analgesic activity in such human can be achieved wherein said ibuprofen present is the (S)(+)-enantiomer form separated from its (R)(−)-form by conventional optical resolution.

13. The method of claim 12 wherein said conventional optical resolution comprises recrystallization and subsequent purification of less soluble diasterioisomers.

14. A method of administering a pharmacological composition adapted to quickly achieve a high concentration in the blood of a human experiencing pain upon administration of said composition, said composition comprising a dosage amount of (S)(+)-ibuprofen effective to quickly achieve a high concentration thereof in the blood of such human, said enantiomer having been separated from its (R)(−)-form by conventional optical resolution.

15. The method of claim 14 wherein said conventional optical resolution comprises recrystallization and subsequent purification of less soluble diasterioisomers.

16. A method of achieving ibuprofen analgesia while minimizing unwanted side effects as compared to administration of a racemic mixture of ibuprofen in a human experiencing pain, comprising administering to such human (S)(+)-ibuprofen free from the (R)(−)-enantiomer to achieve analgesia with a minimization of unwanted side effects from the presence of the (R)(−)-enantiomer.

17. A method of achieving analgesia in a human experiencing pain while minimizing unwanted side effects comprising administering to such human (S)(+)-ibuprofen free from the (R)(−)-enantiomer at a dosage level of one half or less as compared with a dosage of racemic ibuprofen which comprises (S)(+)- and (R)(−)-ibuprofen to achieve comparable analgesia effect with less unwanted side effects.

18. The method according to claim 17 wherein the unwanted side effect is selected from the group consisting of gastro-intestinal tract effects, stomach ulcer formation, diarrhea, sodium retention, oedema formation, kidney damage, central nervous system effects and respiratory tract effects.

19. The method of eliciting an onset-hastened and enhanced analgesic response in a human mammal suffering from pain and in need of such treatment, comprising administering to such organism a dosage onset-hastening/enhancing analgesically effective amount of the (S)(+) ibuprofen enantiomer, said enantiomer being present in purified form sufficient to achieve said response.

20. A pharmaceutical composition of matter adapted to elicit a onset-hastened analgesic response in a mammalian organism in need of such treatment, said composition comprising a solid-state dosage onset-hastening/enhancing analgesically effective amount of the (S)(+) ibuprofen enantiomer, said enantiomer being present in purified form sufficient to achieve said response, and a nontoxic pharmaceutically acceptable carrier or diluent therefor.

21. A method of achieving the response of quick analgesia and greater analgesic activity in a human experiencing pain comprising administering to such human a dosage amount of (S)(+)-ibuprofen enantiomer effective to achieve quick analgesia and greater analgesic activity in such human, said enantiomer being present in purified form sufficient to achieve said response.

22. A pharmacological composition adapted to achieve the response of quick analgesia and greater analgesic activity in a human experiencing pain, said composition comprising a dosage of an amount of (S)(+)-ibuprofen enantiomer effective to achieve quick analgesia and greater analgesic activity in such human, said enantiomer being present in purified form sufficient to achieve said response, and a suitable carrier or diluent therefor.

23. A pharmacological analgesic composition adapted to quickly achieve the response of a high concentration in the blood of a human experiencing pain upon administration of said composition, said composition comprising a dosage amount of (S)(+)-ibuprofen enantiomer effective to quickly achieve a high concentration thereof in the blood of such human, said enantiomer being present in purified form sufficient to achieve said response.

24. A method of administering a pharmacological composition adapted to quickly achieve the response of a high concentration in the blood of a human experiencing pain upon administration of said composition, said composition comprising a dosage amount of (S)(+)-ibuprofen effective to quickly achieve a high concentration thereof in the blood of such human, said enantiomer being present in purified form sufficient to achieve said response.

* * * * *

UNITED STATES PATENT AND TRADEMARK OFFICE
CERTIFICATE OF CORRECTION

PATENT NO.   : 5,519,057
DATED        : May 21, 1996
INVENTOR(S)  : Dieter Loew, Otto Schuster, H. Lukas It is certified that error appears in the above-identified patent and that said Letters Patent is hereby corrected as shown below:

Column 4, Line 66: change "vaseline" to "petroleum jelly"

Signed and Sealed this

Eleventh Day of July, 2000

*Attest:*

Q. TODD DICKINSON

*Attesting Officer*          *Director of Patents and Trademarks*